United States Patent [19]
Gauthier

[11] 3,932,643
[45] Jan. 13, 1976

[54] PHENANTHRIDINES AND PHENANTHRIDINONES AS ANTIVIRAL AGENTS

[75] Inventor: George J. Gauthier, Mystic, Conn.

[73] Assignee: Pfizer Inc., New York, N.Y.

[22] Filed: June 7, 1974

[21] Appl. No.: 477,529

Related U.S. Application Data

[62] Division of Ser. No. 431,255, Jan. 7, 1974, Pat. No. 3,838,134, which is a division of Ser. No. 240,830, April 3, 1972, Pat. No. 3,838,131.

[52] U.S. Cl. ............................................. 424/258
[51] Int. Cl.² ......................................... A61K 31/47
[58] Field of Search ................................... 424/258

[56] References Cited

UNITED STATES PATENTS

| | | | |
|---|---|---|---|
| 3,573,312 | 4/1971 | Krimmel | 424/258 |
| 3,641,032 | 2/1972 | Rockaway et al. | 424/258 |

*Primary Examiner*—Sam Rosen
*Attorney, Agent, or Firm*—Francis X. Murphy; Charles J. Knuth; Albert E. Frost

[57] ABSTRACT

Phenanthridines and phenanthridinones of the formulae

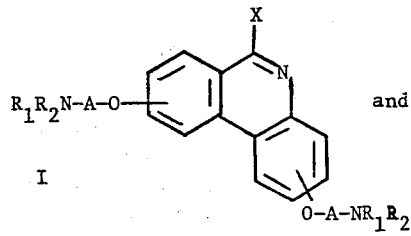

and the pharmaceutically-acceptable acid addition salts thereof wherein X is chloro, bromo, hydroxy, alkoxy having from 1 to 6 carbon atoms, amino, monoalkylamino, dialkylamino wherein each of the alkyl groups has from 1 to 6 carbon atoms, and benzylamino; R is hydrogen, alkyl having from 1 to 6 carbon atoms, $-A-NR_1R_2$ wherein each of $R_1$ and $R_2$ is alkyl having from 1 to 6 carbon atoms and A is a divalent alkylene radical having from 2 to 6 carbon atoms; and each of Y and Z is hydrogen, and ω-dialkylaminoalkoxy wherein the alkyl and alkoxy groups have from 1 to 6 carbon atoms, and from 2 to 6 carbon atoms, respectively; with the proviso that when R is hydrogen or alkyl, each of Y and Z is dialkylaminoalkoxy; useful as antiviral agents and/or interferon inducers and methods for their preparation.

11 Claims, No Drawings

PHENANTHRIDINES AND PHENANTHRIDINONES AS ANTIVIRAL AGENTS

CROSS-REFERENCE TO RELATED APPLICATIONS

This application is a division of U.S. application Ser. No. 431,255, filed Jan. 7, 1974, now U.S. Pat. No. 3,838,134, issued Sept. 24, 1974, which in turn is a divisional of U.S. application Ser. No. 240,830, filed Apr. 3, 1972 now U.S. Pat. No. 3,838,131, issued Sept. 24, 1974.

BACKGROUND OF THE INVENTION

1. Field of the Invention

This invention relates to novel phenanthridines and phenanthridinones, to methods for their production, and to their use as intermediates and/or antiviral agents and as agents for stimulating interferon production of animals. More particularly, it relates to the control of virus infections in animals and to the induction of interferon in animals by oral parenteral, intranasal or topical adminstration of a mono- or bis-substituted[ω-(di-lower alkyl)aminoalkoxy]phenanthridine or phenanthridinone.

2. Description of the Prior Art

The cells of vertebrates produce, in response to virus infection, a substance which enables cells to resist the multiplication of a variety of viruses. The viral-resisting or viral-interfering substances are referred to as "interferons." They are a heterogeneous group of antiviral proteins which vary quite widely in their molecular weights. Although such proteins may differ in their physico-chemical properties, they all exhibit the same biological properties; namely, they inhibit a wide range of unrelated viruses, have no toxic or other deleterious effects on the cells and are species-specific (Lockart, *Frontiers of Biology*, Vol.2, "Interferons," edited by Fintner, W. B. Saunder Company, Philadelphia, 1966, pp. 19–20).

The discovery of interferon by Isaacs and Lindenmann in 1957 (*Proc. Roy. Soc. B.*, 147, 258–267) gave rise to great optimism that an economic preparation of exogeneous interferon might be developed for routine clinical use against viral infections. However, despite great expenditures of effort and money, no safe, effective economical source has yet been developed. An alternate approach to producing interferon has, therefore, been pursued. This approach comprises administering to the animal to be protected, or treated, a non-viral substance which stimulates—or induces—production of interferon in the cells. The interferon produced in this fashion is referred to as "endogenous" interferon.

The discovery of antiviral compounds is far more complicated and difficult than is the discovery of antibacterial and antifungal agents. This is due, in part, to the close structural similarity of viruses and the structures of certain essential cellular components, such as ribonucleic and deoxyribonucelic acids, and to the difficulty of establishing suitable tests for evaluating antiviral agents. However, despite these difficulties, numerous non-viral substances have been found capable of stimulating or inducing interferon formation in animals. Included among such substances are bacteria, parasites, bacterial endotoxins, pyran copolymers, helenine, phytohemagglutinin, polyacrylic compounds, nucleic acids and polynucleotides. Use of these inducers is, however, objected to for one or more reasons, e.g., toxicity, antigenicity, infectiousness, and their routine clinical use appears remote (Zhdanov et al., *Internat'l. Virol. I.* 1st Int. Congr. Virol. Helsinki 1968, S. Karger, New York, pp. 100–1, 1969).

More recently 2,7-bis[2-(diethylamino)ethoxy]fluoren-9-one dyhydrochloride, a purely synthetic material of relatively low molecular weight, has been reported to be an oral inducer of interferon in mice (*Abstracts Federation Proceedings*, Vol. 29, No. 2, page 635, 1970; Abstracts 2189 and 2190).

A variety of "antiviral agents" are described in the literature. These have been summarized by Osdene in "Topics in Medicinal Chemistry," edited by Rabinowitz and Meyerson, Interscience Publishers, New York, 1968, pages 141–176. For the purpose of his review, Osdene has made use of Herrmann's definition of "antiviral agent" (Herrmann et al., *Proc. Soc. Exptl. Biol. Med.* 103, 635, 1960); namely, an agent "which can produce either a protective or therapeutic effect to clear detectable advantage of the virus-infected host, or any material that can significantly enhance antibody formation, improve antibody activity, improve non-specific resitance, speed convalescence or depress symptoms." This definition is of such breadth as to cover both prophylactic and therapeutic agents. It includes substances such as interferon, and a host of synthetic materials, such as 1-adamantanamine, pyrimidines, biguanides, guanidine, pteridines, to mention a few. It is noted that such synthetic materials are antiviral agents. They are not interferon inducers but operate by a totally different mechanism. Interferon inducers may, of course, be referred to as antiviral agents. The converse, however, is not necessarily true.

Virus infections which attack animals, including man, are normally contagious afflictions which may spread so rapidly that they can reach explosive, epidemic proportions in relatively short periods of time. In the past, many of these epidemics have resulted in large numbers of deaths and have been responsible to huge economic losses. Obviously, a method of reducing the incidence of these viral infections, such as the method of this invention, would be a valuable addition to the armamentarium of medical technology.

SUMMARY OF THE INVENTION

It has now been found that certain phenanthridines and phenanthridinones are effective antiviral agents in vertebrate animals when administered orally, parenterally, intranasally or topically to the animals. Further, many of these compounds are effective inducers of endogenous interferon in animals when administered to the animals via the above mentioned routes. The novel antiviral agents of this invention have the formulae

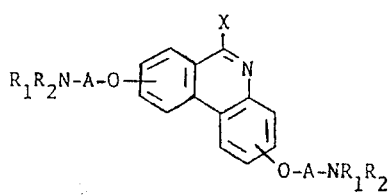

I and

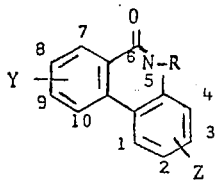

II wherein X is selected from the group consisting of chloro, bromo, hydroxy, alkoxy containing from 1 to 6 carbon atoms, amino, monoaklylamino, dialkylamino wherein each of the alkyl groups contains from 1 to 6 carbon atoms, and benzylamino;

R is selected from the group consisting of hydrogen, alkyl containing from 1 to 6 carbon atoms, $-A-NR_1R_2$ wherein each of $R_1$ and $R_2$ is alkyl containing from 1 to 6 carbon atoms and A is a divalent alkylene radical containing from 2 to 6 carbon atoms;

each of Y and Z is selected from the group consisting of hydrogen, and ω-dialkylaminoalkoxy wherein the alkyl and alkoxy groups contains from 1 to 6 carbon atoms, and from 2 to 6 carbon atoms, respectively;

with the proviso that when R is hydrogen or alkyl, each of Y and Z is ω-dialkylaminoalkoxy.

Also included within the purview of this invention are compounds of formula II wherein R is hydrogen. Such compounds serve as intermediates for compounds of formula II wherein R is alkyl or $-A-NR_1R_2$ and for compounds of formula I wherein X is other than hydroxy, as described and exemplified below.

It is recognized, of course, that compounds of formula I wherein X is hydroxy exist in tautomeric equilibrium with compounds of formula II wherein R is hydrogen. The numbering system used in the above formulae is that of Chemical Abstracts.

Of the lower alkoxy, lower alkyl and carbo(lower alkyl) groups, those having up to six carbon atoms in the alkoxy and alkyl groups are preferred since the starting materials are more readily available than are those containing a greater number of carbon atoms.

Also included in this invention are the pharmaceutically-acceptable acid addition salts of the compounds described herein. The term "pharmaceutically-acceptable" acid addition salts is intended to include salts formed with inorganic and orgaic acids. Representative of such salts are the water-soluble and water-insoluble salts, such as the hydrochloride, hydrobromide, phosphate, nitrate, sulfate, acetate, hexafluorophosphate, citrate, gluconate benzonate, propionate, butyrate, sulfosaliculate, maleate, laurate, malate, fumarate, succinate, oxalate, tartrate, amsonate (4,4-diaminostilbene-2,2'-disulfonate), pamoate (1,1-methylene-bis-2-hydroxy-3-naphthoate), stearate, 3-hydroxy-2-naphthoate, p-toluenesulfonate, picrate, lactate and suramin salt.

The compounds described herein exhibit, by virtue of their ability to induce production of endogenous interferon in animals, broad-spectrum activity against a variety in vivo when administered orally, parenterally, (subcutaneously, intramuscularly, intraperitoneally, intranasally (e.g., by inhalation or spray) or topically. This usefulness is primarily one of prophylactic rather than of therapeutic control of virus infections. They do not produce interferon in tissue culture, but only in vivo and can, therefore, be considered as stimulators of host defense mechanisms.

Further, these compounds stimulate the animal body to produce interferon when administered along and/or in combination with an otherwise inactive, single-stranded ribonucleic acid, such as highly polymerized ribonucleic acid from yeast, yeast nucleic acid (calbiochem 55712, Calbiochem, Los Angeles, California). Those compounds wihch induce interferon when administered along are given at considerably lower doses when given in combination with the single-stranded ribonucleic acid. Unique as inducers of interferon when used alone are compounds of formula II wherein one of Y and Z is hydrogen and the other is ω-di(lower alkyl)aminoalkoxy and R is ω-di(lower alkyl)aminoalkyl; that is, $-A-NR_1R_2$, wherein each of alkyl and alkoxy contain from 2 to 4 carbon atoms; and those of formulae I and II wherein each of Y and Z is ω-di(lower alkyl)aminoalkoxy wherein the alkyl and alkoxy moieties contain from 2 to 4 carbon atoms.

DETAILED DESCRIPTION OF THE INVENTION

The novel compounds of this invention can be prepared by several methods, such as those described by Walls in *Heterocyclic Chemistry* 4, Ch. 4 (1952), John Wiley & Sons, Inc. N.Y. and by Keene et al., in *Advances in Heterocyclic Chemistry* 13, 317–369 (1971), Academic Press, N.Y.

An especially useful method comprises ring expansion of an appropriate Y,Z-substituted fluoren-9-one by the Schmidt or Beckmann reactions. The Schmidt reaction involves the reaction of a fluoren-9-one with hydrazoic acid in the presence of a strong mineral acid. In the usual procedure, a solution of hydrazoic acid in benzene and chloroform or, alternatively and preferably, an aqueous solution of sodium azide, is gradually added to a stirred solution of the fluoren-9-one in concentrated sulfuric acid at a temperature of from about 0° to about 25° C. Aqueous sodium azide is favored over hydrozoic acid for reasons of convenience, ease of handling and reduced hazards. The reaction is generally run at 0° to 10° C. during addition of the sodium aside or hydrazoic zcid, and then at about room temperature until evolution of nitrogen ceases. The exothermic nature of the reaction necessitates, in most instances, the use of a cooling bath coupled with further temperature control by regulating the rate of addition of the hydrazoic acid or sodium azide solutions. Higher or lower temperatures can be, and are used, if the particular fluoren-9-one reacts sluggishly or if it reacts so rapidly as to render temperature control difficult.

Concentrated sulfuric acid is used as solvent and catalyst. It is favored over other, e.g., hydrochloric acid, polyphosphoric acid, phosphorous trichloride or pentachloride sulfonic acids and phosphoric, acids because of the improved yields of phenanthridinones it affords. The ratio of the sulfuric acid to hydrozoic acid or sodium azide is not critical. However, the sulfuric acis is used in excess. When hydrazoic acid itself is employed as reactant, from about 2 to about 10 ml. of sulfuric acid used per gram of fluoren-9-one reactant. When aqueous sodium azide is the hydrazoic acid source from about 2 to about 20 ml. of sulfuric acid are used per gram of fluoren-9-one reactant.

The order of addition of reactants appears to have little, if any, effect on the overall reaction. In addition to the above procedure, a mixture of the fluoren-9-one compound and hydrazoic acid (or sodium azide) is added to concentrated sulfuric acid or concentrated acid-benzene (or chloroform). In still another procedure, the concentrated sulfuric acid is added gradually to a mixture of the fluoren-9-one and hydrazoic acid in benzene (or chloroform). These two procedures are sometimes used when hydrazoic acid rather than sodium azide is employed as reactant.

The molar ratio of hydrazoic acid or of sodium hydrazide to fluoren-9-one reactant is likewise not critical, but should, of course, be at least 1:1. In practice, a molar ratio of from about 1.2:1.0 to about 3.0:1.0 has been found especially useful and productive of satisfactory yields of desired product.

The reaction is run until evolution of gas ceases. In the laboratory it has been convenient to stir the reaction mixture for several hours, e.g., 5 to 7 hours, in an ice bath following addition of the hydrazoic acid or sodium azide solution to the fluoren-9-one, followed by stirring overnight at room temperature.

The products are isolated by pouring the reaction mixture over a large volume of wet ice, adjusting the pH of the resulting solution to about 8.0 to 9.0 with aqueous sodium hydroxide and extracting the basic solution with diethyl ether. Removal of the ether provides the product which is purified by conventional methods, such as recrystallization from a suitable solvent.

The Beckmann rearrangement reaction is of value in the preparation of 3,8-disubstituted-6(5H)-phenanthridinones in which the substituents are identical. The reaction involves rearrangement of the appropriate 2,7-disubstituted fluoren-9-one oxime in polyphosphoric acid at an elevated temperature. The general procedure comprises heating the fluoren-9-one oxime in 40–50 times its weight of polyphosphoric acid at from about 180° C. to about 225° C. for periods of 0.1 to 0.5 hour. The mixture is then cooled, triturated in water, and the product separated by filtration and purified by conventional methods, e.g., recrystallization from a suitable solvent.

The necessary oxime reactants are prepared in the conventional manner by treating the appropriate fluoren-9-one with two equivalents of hydroxylamine hydrochloride in refluxing 70% ethanol. Alternatively, and preferably, they are prepared by treating a solution of the fluoren-9-one in dimethylsulfoxide with a 10% excess of hydroxylamine hydrochloride dissolved in the minimum volume of water. The reaction mixture is heated on a steam bath for 10 minutes, or longer is necessary, and then cooled and poured into water. The oxime is isolated and recrystallized from a suitable solvent such as ethanol or ethanol-water.

Of these two reactions, the Schmidt reaction is preferred since it is of wider applicability than is the Beckmann rearrangement which requires preparation of the intermediate fluoren-9-one oxime and is of practical preparative value only for those phenanthridinones wherein the Y and Z substituents are identical.

Compounds of this invention of formulae I and II can also be prepared from phenanthridines and phenanthridinones according to known procedures. Compounds wherein Y and/or Z is di(lower alkylamino)alkoxy can be prepared by alkylating the precursor hydroxy phenanthridine or hydroxy phenanthridinone the appropriate chloro (or bromo) dialkylamine compound in a reaction-inert solvent (N,N-dimethylformamide, tetrahydrofuran, dioxan at a temperature of from about 0° C to about 30° C. in the presence of sodium hydride or other suitable base, e.g., sodium or potassium hydroxide, amide, methoxide or ethoxide. The sodium or potassium salt can be preformed rather than formed in situ, as is described in U.S. Pat. No. 2,732,373.

The phenanthridinone compounds of formula II wherein R is hydrogen serve as intermediates for the preparation of compounds of formula II wherein R is alkyl or $-A-NR_1R_2$, and for compounds of formula I wherein X is other than hydroxy as previously noted. The appropriate phenanthridinone compounds is heated at an elevated temperature, that is, from about 150° C. to about 200° C. with two to five times its weight of a phosphoryl halide, such as phosphorous oxychloride, in the presence or absence of phosphorous pentachloride for from 1 to 6 hours. The 6-chlorophenanthridine thus produced is isolated from the reaction mixture by crystallization and decolorization using a suitable solvent such as benzene, toluene, xylene, chloroform or carbon tetrachloride.

The 6-chloro (or bromo) phenanthridine is then converted by appropriate procedures of formula I compounds wherein X is lower alkoxy, amino or substituted amino. The 6-halo atom is replaced with lower alkoxy by treatment with the appropriate sodium alkoxide generally in a refluxing solution of the alcohol corresponding to the lower alkoxide. Replacement of the 6-halo to by amino or substituted is accomplished by treating the 6-halo compound with an excess of ammonia or the appropriate amine at an elevated temperature, e.g., 100°–175° C., under pressure; that is, in a steel bomb or other suitable pressure vessel. The reaction can also be carried out at atmospheric pressure by refluxing the 6-halo compound and an excess of the appropriate amine in a suitable solvent, such as ethanol, n-propanol, n-butanol, benzene, hexane, dioxane, for up to 48 hours. The products are recovered by known methods. This procedure is especially valuable for compounds wherein X is benzylamino.

Compounds of formula II wherein R is other than hydrogen are prepared by nucleophilic reaction of the anionic form of the appropriate formula II compound (R=H) with the appropriate halo reactant (halo-R). Sodium hydride serves as an excellent base for generating the reactive anion. The reaction is conducted in N,N-dimethylformamide or other suitable solvent at from about 20° C. to about 40° C. for from four to about twenty hours. The products are recovered by known procedures.

Alternatively, compounds wherein R is methyl are readily prepared by using excess dimethylsulfate as methyating agent in N,N-dimethylformamide or other suitable solvent in the presence of potassium carbonate at a temperature of from about 50° C. to the reflux temperature of the reaction mixture.

Acid addition salts of the compounds described herein are prepared by conventional procedures, as by mixing the compound in a suitable solvent with at least an equimolar amount of the required acid and recovering the salt by evaporation, or by precipitation by addition of a non-solvent for the salt. Hydrochloride salts are readily prepared by passing dry hydrogen chloride through a solution of the amine compound in an organic solvent such as ether.

The antiviral activity of the above described compounds is determined by the following procedures. In the first procedure, the test compound is administered to mice by the oral or intraperitoneal route eighteen to twenty-four hours prior to challenging the mice with a lethal dose of encephalomyocarditis virus and determining the survival rate 10 days after the challenge.

The procedure in which the drug is given eighteen to twenty-four hours before, and at a distinctly different site from virus injection, is designed to eliminate local effects between the drug and virus, and select only compound which produce a systemic interferon response.

The second general procedure discriminates between compounds which exhibit antiviral activity in the first procedure for their ability to produce an antiviral state in mice as indicated by their ability to stimulate circulating interferon after oral or parenteral administration. In both procedures, the test compounds are administered alone and in combination with from about 2 to about 20 times by weight of an otherwise inactive (noninducer of interferon and non-antiviral), single-stranded, highly-polymerized ribonucleic acid from yeast, yeast nucleic acid.

Oral, parenteral, topical and intranasal administration of the above-described compounds to an animal, including man, before exposure of the animal to an infectious virus provide rapid resitance to the virus. The resistance engendered is non-specific and is effective against a great number of viruses. Such administration is effective when given as much as seven days prior to exposure to the virus. Preferably, however, administration should take place from about three days to about one day before exposure to the virus, although this will vary somewhat with the particular animal species and the particular infectious virus.

When administered orally, the compounds are used at a level of from about 5 mg./kg. to about 300 mg./kg. and, preferably, at a level of from about 10 mg./kg. to 200 mg./kg.

When administered parenterally, the compounds of this invention are used at a level of from about 1 mg./kg. of body weight to about 250 mg./kg. of body weight. The favored range is from about 5mg./kg. to about 100 mg./kg. of body weight, and the preferred range from about 5 mg./kg. to about 50 mg./kg. of body weight. The dosage, of course, is dependent upon the animal being treated and the particular compound involved, and is to be determined by the individual responsible for its adminsitration. Generally, small doses will be administered initially with gradual increase in dosage until the optimal dosage level is determined for the particular subject under treatment.

Intraperitoneal injection are the preferred method of parenteral injection for several reasons: simplicity, convenience and the compounds appear less toxic. Vehicles suitable for parenteral injection may be either aqueous, such as water, isotonic saline, isotonic dextrose, Ringer's solution; or non-aqueous, such as fatty oils of vegetable origin (cottonseed, peanut oil, corn, sesame), and other non-aqueous vehicles which will not interfere with the efficacy of the preparation and are non-toxic in the volume or proportion used (glycerol, ethanol, propylene, glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol.

When the compounds of this invention are administered, they are most easily and economically used in a dispersed form in an acceptable carrier. When it is said that the compound is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the inducer with the respiratory tract of the animal. Effective methods include administration of the inducer by intranasal or nasopharyngeal drops and by inhalation as delivered by a nebulizer or an aerosol. Such methods of administration are of practical importance because they provide an easy, safe and efficient method of practicing this invention. For intranasal administration of the inducer, usually in an acceptable carrier, a concentration of inducer between 1.0 mg/ml. and 100 mg./ml. is satisfactory. Concentrations in the range of about 30 to 50 mg./ml. allow administration of a convenient volume of material.

For topical application, the inducers are most conveniently used in an acceptable carrier to permit ease and control of application and better absorption. Here also concentrations in the range of from about 1.0 mg./ml. to about 250 mg/ml. are satisfactory. In general, in the above two methods of administration a dose within the range of about 1.0 mg./kg. to about 250 mg./kg. of body weight and, preferably, from about 5.0 mg./kg. to about 50 mg./kg. of body weight will be administered.

The compounds employed in this invention may be employed alone; i.e., without other medicinals, as mixtures of more than one of the herein described compounds or in combination with other medicinal agents, such as analgesics, anesthetics, antiseptics, decongestants, antibiotics, vaccines, buffering agents and inorganic salts, to afford desirable pharmacological properties. Further, they may be administered parenterally in combination with hyaluronidase to avoid or, at least; to minimize local irritation and to increase the rate of absorption of the compound. Hyaluronidase levels of at least about 150 (U.S.P) units are efffective in this respect although higher or lower levels can, of course, be used.

Those compounds or materials of this invention which are water-insoluble, including those which are of low and/or difficult solubility in water, are for optimum results administered in formulations, e.g., suspensions, emulsions, which permit formation of particle sizes of less than about 20 $\mu$. The particle sizes of the formulations influence their biological activity apparently through better absorption of the active materials. In formulating these materials, various surface active agents and protective colloids are used. Suitable surface active agents and the partial esters of common fatty acids, such as lauric, oleic, stearic, with hexitol anhydrides derived from sorbitol, and the polyoxyethylene derivatives of such ester products. Such products are sold under the trademarks "Spans" and "Tweens," respectively, and are available from the Atlas Powder Co., Wilmington, Delaware. Cellulose ethers, especially cellulose methyl ether (Methocel, available from the Dow Chemical Co., Midland, Michigan) are highly efficient as protective colloids for use in emulsions containing the materials of this invention.

The water-soluble compounds described herein are administered for optimum results in aqueous solution.

The production of interferon by the administration of compounds described herein is demonstrated by the protection of animals, generally mice as the initial test animal, against viral infections. Encephalomyocarditis virus is a convenient test organism. The challenge virus is prepared by inoculating mice for at least five passages with neurotropic strain of encephalomyocarditis virus (infected mouse brain). A 10% suspension of infected brain tissues is prepared from infected mice and stored at −70° C. until needed (Takano et al., J. Bact. 90, 1542, 1965). It is titrated to a dose which will case death in five to seven days after challenge to unprotected animals. It is given subcutaneously into the neck scruff. The appropriate dose in contained in 0.1 ml. In general, the dose administered to the animals is from 10 to 25 times the $LD_{50}$ (the dose which causes the death of 50 percent of the animals).

For determination of antiviral activity, mice are adminstered the test compound orally at levels of 200 mg./kg. and 40 mg./kg. of body weight 18 to 20 hours prior to virus challenge and the number of survivors determined ten days after challenge.

Alternatively, the mice are parenterally (intraperitoneally) injected with the test compound at levels of 5 or 10 mg./kg. and 50 mg./kg. of body weight eighteen to twenty hours prior to virus challenge and the number of survivors determined ten days after challenge. Interferon production is monitored following administration of the test compound according to the procedure described by Wheelock, *Proc. Soc. Exptl. Biol. Med.* 124, 855–85 (1967).

Once interferon induction by a given compound is observed, the compound is administered to the test animal at various time intervals prior to challenge, e.g., 6, 36, 48 and 72 hours; and by other parenteral routes, e.g., intramuscular and subcutaneous.

Interferon induction is determined using female albino Swiss mice (Charles-River) as the test animal. Mice weighing 20 to 25 grams are housed in groups of five and are given food and water ad libitum. The test compound is evaluated at 200 mg./kg. and 40 mg./kg. of body weight, and given in a single oral dose eighteen to twenty hours prior to bleeding. The mice are bled under ether anestesia from teh bracheal artery, the blood collected in heparinized pipettes and tubes, and the pooled plasma from the five mice prepared by contrifugation of the blood for thirty minutes at 2,000 rpm. Dilutions of the plasma are pipetted into plastic tubes containing sheet of L-929 mouse fibroblasts (available from Flow Laboratories, Rockville, Maryland). These latter are twenty-four hour cultures in L-15 media containing 10% fetal calf serum and antibiotics (available from Grand Island Biological Company, Grand Island, New York). The cultures are grown from initial plantings of 1 ml. of 100,000 cells/ml. After twenty-four hours of incubation with the plasma, the cultures are washed with media and challanged with 0.2 ml. of a dilution of vesicular stomatitis virus titrated to produce a complete destruction of the cell sheets in 24 to 48 hours. The cultures are in contact with the virus dilution in protein-free media for one hour to allow the virus to adsorb to the cells, and then the tubes receive 1 ml. of complete media. After 25 to 48 hours of incubation at 37° C., the tubes are scored by cytopathogenic effect of the virus and compared with standard interferon samples. Interferon units are recorded as the reciprocal of the plasma concentration which affords 50% protection to the cell sheets.

The antiviral activity of 3,8-bis[($\beta$-diethylamino)ethoxy]-6(5H)-phenanthridinone is determined using female albino Swiss mice (Charles-River) as the test animal. Mice weighing from 20 to 25 grams are housed in groups of five, and are given food and water ad libitum. The test compound in phosphate buffered saline is evaluated at two dose levels (40 mg./kg. and 200 mg./kg. of body weight) and given orally in a single dose 18 to 20 hours prior to virus challenge. On the following day (18 to 20 hours post injection), the mice are challenged subcutaneously with an 0.2 ml. injection of encephalomyocarditis virus at a dilution titrated to give a five- to six-day death endpoint in unprotected animals. Survival data is recorded for the subsequent ten days and the ten day survival is used as an index of efficiency. Validity of each test is established by the inclusion of unprotected groups and groups receiving 2,7-bis-[2-diethylamino)ethoxy]fluoren-9-one, 200 and 40 mg./kg. for positive control.

Alternatively, the compounds are evaluated by intraperitoneal administration in the above tests for interferon induction and antiviral activity at dose levels of 5 mg./kg. and 50 mg./kg. of body weight. The test compound is administered in a single dose of 0.5 ml. A representative formulation containing 5-[($\beta$-diethylamino)ethyl]-9-[($\beta$-diethylamino)ethoxy]-6(5H)-phenanthridinone as test compound is exemplified.

A mixture of the inducer (100 mg.) and polysorbate 80 (Tween 80; 0.1 ml.) is heated in a boiling water bath. The test compound is completely miscible with the polysorbate 80. To this mixture is then added with vigorous vortexing 2.5 ml. of the following composition, previously warmed to about 55° C:

| | |
|---|---|
| Methocel-15 (Dow Chemical Co.) | 0.50 g. |
| Tween 80 | 1.00 g. |
| CMC-70* | 10.00 g. |
| Sodium chloride | 9.00 g. |
| Distilled water | 984.80 g. |

*Sodium carboxymethyl cellulose available from Hercules Powder Co., Wilmington, Delaware.

Then 7.28 ml. of a 0.14M sodium chloride-0.01M sodium phosphate solution of pH 7.0 warmed at 55° C. is added with continued vigorous vortexing. The formulation thus produced contains 10 mg. of inducer per ml. of suspension.

The hydrochloride salt of 3,8-bis[($\beta$-diethylamino)ethoxy]-6(5H)-phenanthridinone is readily formulated by vigorous vortexing of the salt in hot 0.14M sodium chloride-0.01M sodium phosphate of pH 7.0.

In this manner, 3,8-bis[($\beta$-diethylamino)ehtoxy]-6(5H)-phenanthridinone when administered orally to mice at 200 and 40 mg./kg. of body weight, was found to achieve 72% and 28% survival rates, respectively. 3,8-bis[($\beta$-diisopropylamino-ethoxy]-6(5H)-phenanthridinone produced survival rates of 43% and 14%, respectively, at the same dosage levels. The N-substituted compounds of formula II: 3-[($\beta$-diethylamino)ethoxy]-5-[($\beta$-diethylamino)ethyl]-6(5H)-phenanethridinone and 5-[($\beta$-diethylamino)ethyl]-8-[($\beta$-diethylamino)-ethoxy]-6(5H)-phenanthridinone gave survival rates at 200 mg./kg. levels of 86% and 43%, respectively; and at 40 mg./kg. levels, each achieved 14% survival.

The known antiviral agent, 2,7-bis[2-(diethylamino)ethoxy]fluoren-9-one dihydrochloride, when tested in this manner gave survival rates averaging 93% at 200 mg./kg. and 49% at 40 mg./kg. of body weight.

The water-soluble compounds of the invention are conveniently administered in phosphate buffered saline. The water-insoluble compounds are administered in formulations of the type described above or in various other formulations as previously noted. Dimethylsulfoxide serves as a suitable vehicle for water-insoluble compounds. a representative formulation for such compounds comprises 25 to 100 mg. of the chosen drug, dimethylsulfoxide (1 ml.), polysorbate 80 (1 ml.) and 8 ml. of a composition comprising:

| | |
|---|---|
| Methocel-15 | 0.50 g./l. |
| Polysorbate 80 | 1.00 g./l. |
| CMC-70 | 10.00 g./l. |
| Sodium chloride | 9.00 g./l. |
| Methyl p-hydroxybenzoate | 1.80 g./l. |
| Propyl p-hydroxbenzoate | 0.20 g./l. |
| Distilled water | 984.00 g./l. |

In some instances, as where clumping of the drug particles occurs, sonication is employed to provide a homogeneous system.

EXAMPLE I 3,8-Bis[(β-Diethylamino)ethoxy]-6(5H)-Phenanthridinone

A. via Schmidt Reaction

Sodium azide (1.19 g., 18.3 mM) was added with stirring over a half-hour period to a solution of 2,7-bis[(β-diethylamino)ethoxy]fluoren-9-one (5.0 g., 12.2 mM) in concentrated sulfuric acid (30 ml.). The reaction mixture was then stirred at room temperature until nitrogen was no longer evolved. The reaction mixture was then poured over wet ice (300 ml.) and the pH of the resulting solution adjusted to 8.5–9.0 with 20% aqueous sodium hydroxide. The basic solution was extracted with diethyl ether (2 × 300 ml.) and then with chloroform (2 × 300 ml.). The combined extracts were dried (MgSO₄) and then evaporated under reduced pressure to give 3.37 g. of crude product. The crude product was recrystallized in isopropanol. Yield = 1.19 g., M.P. 150°–152.5° C.

A second crop of product (0.380 g.) was obtained by concentrating the isopropanol filtrate remaining after removal of the main crop.

Analysis: Calc'd. for $C_{25}H_{35}N_3O_3$: C, 70.56; H, 8.29; N, 9.87%. Found: C, 70.57; H, 7.91; N, 9.87%.

B. Via Beckmann Rearrangement

To a stirred mixture of phosphorous pentoxide (2 g.) and polyphosphoric acid (10 g.) at 50° C. was added the oxime of 2,7-bis[(βdiethylamino)ethoxy]fluoren-9-one (213 mg., 1 mM). The temperature was raised to 100° C–120° C. within 10 minutes and stirring and heating continued for 4 hours. The mixture was then poured into water (50 ml.) The aqueous solution was made alkaline with concentrated sodium hydroxide solution to pH 11 and then extracted with ether until the extract was colorless (10 × 75 ml.). The combined ether extracts were dried (Na₂SO₄) and evaporated to give 65 mg. of crude product. It was purified by recrystallization from isopropanol. The product was identical to that of Method A.

In like manner, the following compounds were prepared from the appropriate fluoren-9-one oxime

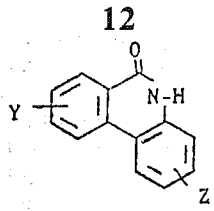

| Position | Y = Z |
|---|---|
| 3,8 | OCH₂CH₂N(CH₃)₂ |
| 3,8 | O(CH₂)₃N(n—C₄H₉)₂ |
| 3,8 | O(CH₂)₆N(C₂H₅)₂ |
| 3,8 | OCH₂CH₂N(n—C₆H₁₃)₂ |
| 3,9 | OCH₂CH₂N(C₂H₅)₂ |

EXAMPLE II 3,8-Bis[(γ-dimethylamino)propoxy]-6(5H)-Phenanthridinone

Following the procedure of Example I but using 2,7-bis[(γ-dimethylamino)propoxy]fluoren-9-one (6.1 g., 16 mM) in place of 2,7-bis[(β-diethylamino)ethoxy]fluoren-9-one; sodium azide (1.56 g., 24 mM), water (32 ml.) and concentrated sulfuric acid (25 ml.), 3,8-bis[(γ-dimethylamino)propxy]-6(5H)-phenanthridinone (525 mg.) was produced; M.P. 193°–195° C.

Analysis: Calcd. for $C_{23}H_{31}N_3O_3$: C, 69.49; H, 7.86; N, 10.57%. Found: C, 68.39; H, 7.69; N, 10.36%.

EXAMPLE III 3,8-Bis[(β-diisopropylamino)ethoxy]-6(5H)-Phenanthridinone

Sodium azide (2.1 g., 32.3 mM), 2,7-bis[(β-diisopropylamino)-ethoxy]fluoren-9-one (10 g., 21.5 mM) and concentrated sulfuric acid (50 ml. were reacted according to the procedure of Example I. The product was extracted from the basic solution with ether rather than with ether followed by chloroform. The ether extract was dried and evaporated to give, after recrystallization of the crude product from isopropanol, 2,7- g. of product. M.P. 154° C.–156° C.

Analysis: Calcd. for $C_{29}H_{43}N_3O_3$: C, 72.31; H, 9.00; N, 8.72%. Found: C, 72.28; H, 8.95; N, 8.62%.

EXAMPLE IV

Repetition of the procedure of Example I but using the appropriate bis[dialkylamino)alkoxy]fluoren-9-one in place of 2,7-bis[(β-diethylamino)alkoxy]fluoren-9-one affords the following compounds:

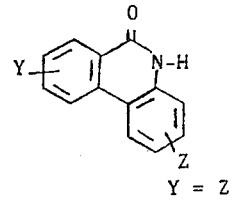

Y = Z

| Position | Y = Z |
|---|---|
| 3,8 | —OCH₂CH₂N(n—C₄H₉)₂ |
| 3,8 | —O(CH₂)₃N(CH₃)₂ |
| 3,8 | —O(CH₂)₃N(C₂H₅)₂ |
| 3,8 | —O(CH₂)₃N(n—C₄H₉)₂ |
| 3,8 | —OCH₂CH₂N(CH₃)(C₂H₅) |
| 3,8 | —OCH₂CH₂N(CH₃)(n—C₄H₉) |
| 3,8 | —OCH₂CH(CH₃)CH₂N(CH₃)₂ |
| 3,8 | —OCH₂CH₂N(n—C₆H₁₃)₂ |
| 3,8 | —OCH₂CH₂N(n—C₃H₇)₂ |
| 3,8 | —O(CH₂)₄N(C₂H₅)₂ |
| 3,10 | —OCH₂CH₂N(C₂H₅)₂ |
| 3,9 | —OCH₂CH₂N(C₂H₅)₂ |
| 2,9 | —OCH₂CH₂N(C₂H₅)₂ |

EXAMPLE V

3-[β-Diethylamino(ethoxy]6(5H)-Phenanthridinone and

8-[(β-Diethylamino)ethoxy]-6(5H)-Phenanthridinone

Sodium azide (1.97 g., 30.5 mM) was added portionwise over a half-hour period to a stirred solution of 2-[(β-diethylamino)ethoxy]fluoren-9-one (6.0 g., 20.3 mM) in concentrated sulfuric acid (30 ml.) at 0° C.–5° C. The mixture was then allowed to warm to room temperature and stirring continued until nitrogen was no longer evolved. The mixture was cautiously poured over wet ice (500 ml.) and the resulting solution made basic (pH 8.5) with 20% aqueous sodium hydroxide. The insoluble yellow precipitate which formed was filtered off. The basic filtrate was extracted with ether until the extracts were colorless. The combined extracts were filtered, dried (MgSO$_4$) and then evaporated to give 4.38 g. of residue. The yellow precipitate was taken up in chloroform, the solution dried (MgSO$_4$) and evaporated to give 2.7 g. of product. The combined solids are dissolved in ethyl acetate and chromatographed on silica. The column is eluted with ethyl acetate and then with ethyl acetate containing increasing amounts of triethylamine. Fractions of eluate were collected and analyzed by thin layer chromatography in the system 5% triethylamine-ethyl acetate. Those fractions showing spots not attributable to the reactants were combined and evaporated to dryness. In this manner, the fraction eluted by ethyl acetate containing 5–15% of triethylamine gave the 8-[(β-diethylamino)ethoxy]-6(5H)-phenanthridinone (2.40 g.) which was recrystallized from ethyl acetate. M.P. 173° C.–178° C.

The fractions eluted with ethyl acetate containing 20% triethylamine gave upon evaporation 3-[(β-diethylamino)ethoxy]-6(5H)-phenanthridinone (820 mg.). It was purified by recrystallization from isopropanol. M.P. 150° C.–155° C.

EXAMPLE VI

The procedure of Example V is followed but using the appropriate 2-[(β-dialkylamino)alkoxy]fluoren-9-one in place of 2-[(β-diethylamino)-ethoxy]fluoren-9-one to produce the compounds below:

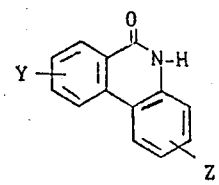

| Y | Z |
|---|---|
| 9—OCH$_2$CH$_2$N(C$_2$H$_5$)$_2$ | H |
| H | 2—OCH$_2$CH$_2$N(C$_2$H$_5$)$_2$ |
| 10—OCH$_2$CH$_2$N(C$_2$H$_5$)$_2$ | H |
| H | 1—OCH$_2$CH$_2$N(C$_2$H$_5$)$_2$ |
| 8—OCH$_2$CH$_2$N(CH$_3$)$_2$ | H |
| H | 3—OCH$_2$CH$_2$N(CH$_3$)$_2$ |
| 9—OCH$_2$CH$_2$N(CH$_3$)$_2$ | H |

-continued

| Y | Z |
|---|---|
| H | 2—OCH$_2$CH$_2$N(CH$_3$)$_2$ |
| 10—OCH$_2$CH$_2$N(CH$_3$)$_2$ | H |
| H | 1—OCH$_2$CH$_2$N(CH$_3$)$_2$ |
| 8—O(CH$_2$)$_3$N(CH$_3$)$_2$ | H |
| H | 3—O(CH$_2$)$_3$N(CH$_3$)$_2$ |
| 9—O(CH$_2$)$_3$N(CH$_3$)$_2$ | H |
| H | 2—O(CH$_2$)$_3$N(CH$_3$)$_2$ |
| 10—O(CH$_2$)$_3$N(CH$_3$)$_2$ | H |
| H | 1—O(CH$_2$)$_3$N(CH$_3$)$_2$ |
| 8—O(CH$_2$)$_2$N(CH$_3$)(C$_2$H$_5$) | H |
| H | 3—O(CH$_2$)$_2$N(CH$_3$)(C$_2$H$_5$) |
| 8—O(CH$_2$)$_2$N(i—C$_3$H$_7$)$_2$ | H |
| H | 3—O(CH$_2$)$_2$N(i—C$_3$H$_7$)$_2$ |
| 8—O(CH$_2$)$_6$N(C$_2$H$_5$)$_2$ | H |
| H | 3—O(CH$_2$)$_6$N(C$_2$H$_5$)$_2$ |
| 8—O(CH$_2$)$_2$N(n—C$_6$H$_{13}$)$_2$ | H |
| H | 3—O(CH$_2$)$_2$N(n—C$_6$H$_{13}$)$_2$ |
| 9—OCH$_2$CH(CH$_3$)CH$_2$N(CH$_3$)$_2$ | H |
| H | 2—OCH$_2$CH(CH$_3$)CH$_2$N(CH$_3$)$_2$ |
| 7—OCH$_2$CH$_2$N(C$_2$H$_5$)$_2$ | H |
| H | 4—OCH$_2$CH$_2$N(C$_2$H$_5$)$_2$ |

EXAMPLE VII 3,8-Bis[(β-Diethylamino)ethoxy]-6-Chloro-Phenanthridine

A mixture of phosphorous oxychloride (80 ml.), phosphorous pentachloride (200 mg., 0.96 mM) and 3,8-bis[(β-diethylamino)ethoxy]-6(5H)-phenanthridinone (2.0 g., 4.7 mM) was heated at reflux for 3 hours. The phosphorous oxychloride was stripped off under reduced pressure and the reside gradually added to chilled concentrated ammonium hydroxide (100 ml.) with stirring. The resulting mixture was extracted with diethyl ether (5 × 100 ml.) and the combined extract washed with water (100 ml.), dried (MgSO$_4$), filtered and evaporated to give 1.63 g. (78%) of product.

Analysis: Calcd. for C$_{25}$H$_{34}$ClN$_3$O$_2$: C, 67.63; H, 7.72; N, 9.46;, Cl, 7.98%. Found: C, 66.63; H, 7.58; N, 9.11; Cl, 8.04%.

EXAMPLE VIII 3,8-Bis[(β-Diisopropylamino(ethoxy]-6-Chloro-Phenanthridine

Phosphorous pentachloride (173 mg., 0.83 mM), phosphorous oxychloride (80 ml.) and 3,8-bis[(β-diisopropylamino(ethoxy]-6(5H)-phenanthridinone (2.0 g., 4.15 mM) were reacted according to the procedure of Example VII to give 1.66 g. of the title product; M.P. 88° C.–91° C.

Analysis: Calcd. for C$_{29}$H$_{42}$ClN$_3$O$_2$: C, 69.64; H, 8.47; N, 8.40%. Found: C, 68,93; H, 8.29; N, 8.17%.

EXAMPLE IX

Repetition of the procedure of Example VII, but using the appropriate bis- and mono-[(β-dialkylamino)alkoxy]-6(5H)-phenanthridinone reactants of Examples II, IV - VI affords the following compounds:

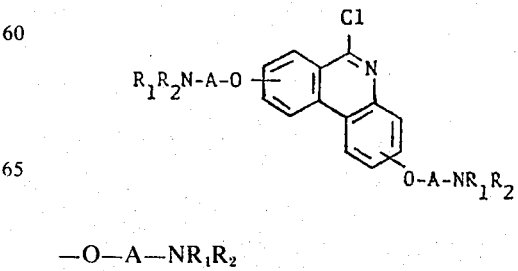

—O—A—NR$_1$R$_2$ 3,8-OCH$_2$CH$_2$N(CH$_3$)$_2$
3,8-OCH$_2$CH$_2$N(n-C$_4$H$_9$)$_2$
3,8-O(CH$_2$)$_3$N(CH$_3$)$_2$
3,8-O(CH$_2$)$_3$N(C$_2$H$_5$)$_2$
3,8-O(CH$_2$)$_3$N(n-C$_4$H$_9$)$_2$
3,8-OCH$_2$CH$_2$N(CH$_3$)(C$_2$H$_5$)
3,8-OCH$_2$CH$_2$N(CH$_3$)(n-C$_4$H$_9$)
3,8-OCH$_2$CH(CH$_3$)CH$_2$N(CH$_3$)$_2$
3,8-OCH$_2$CH$_2$N(n-C$_6$H$_{13}$)$_2$
3,8-OCH$_2$CH$_2$N(n-C$_3$H$_7$)$_2$
3,8-O(CH$_2$)$_6$N(C$_2$H$_5$)$_2$
3,10-OCH$_2$CH$_2$N(C$_2$H$_5$)$_2$
3,9-OCH$_2$CH$_2$N(C$_2$H$_5$)$_2$
2,9-OCH$_2$CH$_2$N(C$_2$H$_5$)$_2$

EXAMPLE X 3,8-Bis[($\beta$-Diethylamino)ethoxy]-6-Diethylaminophenanthridine A mixture of 3,8-bis[($\beta$-diethylamino)ethoxy]-6-chlorophenanthridine (350 mg., 0.79 mM), ethanol (4 ml.) and diethylamine (4 ml.) was heated at 150° C. in a steel bomb for 16 hours and then cooled to room temperature. The reaction mixture was removed from the bomb which was then washed with ethanol (2 × 2 ml.). The combined reaction mixture and washings were evaporated to dryness and the residue partitioned between water and ether. The ether layer was separated, dried (MgSO$_4$) and evaporated under reduced pressure to give 310 mg. of crude product. It was filtered through a silica pad which was then washed with ether (200 ml.) containing 3% thiethylamine and the combined filtrate and wash solution evaporated under reduce pressure. Yield = 260 mg.

Analysis: Calcd. for C$_{29}$H$_{44}$N$_4$O$_2$: C, 72.46; H, 9.23; N, 11.66%. Found: C, 71.77; H, 8.95; N, 11.66%.

EXAMPLE XI 3,8-Bis[($\beta$-Diisopropylamino)ethoxy]-6-Diethylaminophenanthridine A mixture of 3,8-bis[($\beta$-diisopropylamino)ethoxy-9-6-chlorophenanthridine (780 mg., 1.56 mM), ethanol (8 ml.) and diethylamine (8 ml.) was reacted according to the procedure of Example X to give 785 mg. of the title product. The product as obtained by evaporation of the ether solution resulting from the water-ether partition was of sufficient purity that the filtration step of Example X was unnecessary.

Analysis: Calcd. for C$_{33}$H$_{52}$N$_4$O$_2$: C, 73,84; H, 9.76; N, 10.44%. Found: C, 73.58; H, 9.41; N, 9.63%.

EXAMPLE XII 3,8-Bis[($\beta$-Diisopropylamino)ethoxy]-6-Benzylaminophenanthridine A mixture of benzylamine (10 ml.), 3,8-bis[($\beta$-diisopropylamino)-ethoxy]-6-chlorophehnanthridine (780 mg., 1.56 mM) and ethanol) 20 ml.) was refluxed for 2 days. The reaction mixture was then evaporated under reduced pressure and the residue partitioned between ether and water. The ether phase was separated, washed with water, and dried (MgSO$_4$). Removal of the ether under reduced pressure gave 930 mg. of product.

Analysis: Calcd. for: C$_{36}$H$_{50}$N$_4$O$_2$: C, 75.75; H, 8.83; N, 9.82%. Found: C, 74.67; H, 8,34; N, 9.47%.

EXAMPLE XIII 3,8-Bis[($\beta$-Diethylamino)ethoxy]-6-Benzylaminophenanthridine Benzylamine (10 ml.), ethanol (20 ml.) and 3,8-bis[($\beta$-diethylamino)-ethoxy]-6-chlorophenanthridine (350 mg., 0.79 mM) were reacted according to thre procedure of Example XII to give 380 mg. of product.

Analysis: Calcd. for: C$_{32}$H$_{42}$N$_4$O$_2$: C, 74.67; H. 8.22; N, 10.85%. Found: C, 71.55; H, 7.82; N, 9.66%.

EXAMPLE XIV

Following the procedure of Example X and, when X is benzylamino, the procedure of Example XII, the compound listed below are produced from ammonia or the appropriate amines and the products of Examples VII - IX.

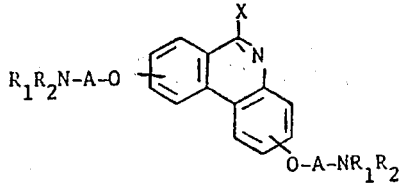

| X | O—A—NR$_1$R$_2$ | X | —O—A—NR$_1$R$_2$ |
|---|---|---|---|
| N(CH$_3$)$_2$ | 3,8—OCH$_2$CH$_2$N(C$_2$H$_5$)$_2$ | NH(C$_7$H$_7$) | 3,8—OCH$_2$CH$_2$N(CH$_3$)(C$_2$H$_5$)$_2$ |
| N(i—C$_3$H$_7$)$_2$ | 3,8—OCH$_2$CH$_2$N(C$_2$H$_5$)$_2$ | N(C$_2$H$_5$)$_2$ | 3,8—OCH$_2$CH$_2$N(CH$_3$)(C$_2$H$_5$)$_2$ |
| N(n—C$_6$H$_{13}$)$_2$ | 3,8—OCH$_2$CH$_2$N(C$_2$H$_5$)$_2$ | NH(C$_7$H$_7$) | 3,8—O(CH$_2$)$_6$N(C$_2$H$_5$)$_2$ |
| N(CH$_3$)$_2$ | 3,8—OCH$_2$CH$_2$N(CH$_3$)$_2$ | N(C$_2$H$_5$)$_2$ | 3,8—O(CH$_2$)$_6$N(C$_2$H$_5$)$_2$ |
| N(CH$_3$)(C$_2$H$_5$) | 3,8—OCH$_2$CH$_2$N(CH$_3$)$_2$ | NH$_2$ | 3,8—O(CH$_2$)$_6$N(C$_2$H$_5$)$_2$ |
| N(n—C$_4$H$_9$)$_2$ | 3,8—OCH$_2$CH$_2$ N(CH$_3$)$_2$ | NH$_2$ | 3,8—OCH$_2$CH$_2$N(n—C$_6$H$_{13}$)$_2$ |
| N(C$_2$H$_5$)$_2$ | 3,8—OCH$_2$CH$_2$N-(n—C$_4$H$_9$)$_2$ | NH(C$_7$H$_7$) | 3,8—OCH$_2$CH$_2$N(n—C$_6$H$_{13}$)$_2$ |
| NH(C$_7$H$_7$) | 3,8—OCH$_2$CH$_2$N-(n—C$_4$H$_9$)$_2$ | N(n—C$_3$H$_7$)$_2$ | 3,8—OCH$_2$CH$_2$N(n—C$_6$H$_{13}$)$_2$ |
| NH$_2$ | 3,8—OCH$_2$CH$_2$N-(n—C$_4$H$_9$)$_2$ | N(CH$_3$)(n—C$_6$H$_{13}$) | 3,8—OCH$_2$CH$_2$N(n—C$_6$H$_{13}$)$_2$ |
| NH$_2$ | 3,8—OCH$_2$CH$_2$N(C$_2$H$_5$)$_2$ | NHC$_7$H$_7$ | 3,10—OCH$_2$CH$_2$N(C$_2$H$_5$)$_2$ |
| NH(CH$_3$) | 3,8—OCH$_2$CH$_2$N(C$_2$H$_5$)$_2$ | N(C$_2$H$_5$)$_2$ | 3,10—OCH$_2$CH$_2$N(C$_2$H$_5$)$_2$ |
| NH(n—C$_3$H$_7$) | 3,8—OCH$_2$CH$_2$N(C$_2$H$_5$)$_2$ | NH$_2$ | 3,9—OCH$_2$CH$_2$N(C$_2$H$_5$)$_2$ |
| N(C$_2$H$_5$)$_2$ | 3,8—O(CH$_2$)$_3$N(C$_2$H$_5$)$_2$ | NH(C$_7$H$_7$) | 3,9—OCH$_2$CH$_2$N(C$_2$H$_5$)$_2$ |
| NH$_2$ | 3,8—O(CH$_2$)$_3$N(C$_2$H$_5$)$_2$ | N(CH$_3$)$_2$ | 3,9—OCH$_2$CH$_2$N(C$_2$H$_5$)$_2$ |
| NHC$_2$H$_5$ | 3,8—O(CH$_2$)$_3$N(C$_2$H$_5$)$_2$ | N(C$_2$H$_5$)$_2$ | 2,9—OCH$_2$CH$_2$N(C$_2$H$_5$)$_2$ |
| NH(n—C$_6$H$_{13}$) | 3,8—O(CH$_2$)$_3$N(C$_2$H$_5$)$_2$ | NH(C$_7$H$_7$) | 2,9—OCH$_2$CH$_2$N(C$_2$H$_5$)$_2$ |
| N(C$_2$H$_5$)$_2$ | 3,8—OCH$_2$CH$_2$N-(n—C$_3$H$_7$)$_2$ | NH$_2$ | 2,9—OCH$_2$CH$_2$N(C$_2$H$_5$)$_2$ |

EXAMPLE XV 3,8-Bis[($\beta$-Diethylamino)ethoxy]-6-Methoxyphenanthridine

A mixture of 3,8-bis[($\beta$-diethylamino)ethoxy]-6-chlorophenanthridine (50 mg., 0.1125 mM), methanol (3 ml.) and sodium methoxide (12.2 mg., 0.225 mM)

was refluxed for one hour at the end of which time additional sodium methoxide (20 mg.) was added. The mixture was refluxed for an additional 23 hours and then evaporated to dryness. The residue was partitioned between water and ether, the ether phase separated, dried (MgSO$_4$) and evaporated under reduced pressure to give 40 mg. of product.

Analysis: Calc. for C$_{26}$H$_{37}$N$_3$½H$_2$O: C, 69,61; H, 8.76; N, 9.37%. Found: C, 69,58; H, 8.01; N, 9.20%.

EXAMPLE XVI

6-Alkoxy Substituted Phenanthridines

Repetition of the procedure of Example XV but using the appropriate sodium alkoxide and the appropriate 6-chloro (or bromo) substituted phenanthridines of Examples VII–IX and, as solvent, the alcohol corresponding to the akloxide, the following compounds are produced.

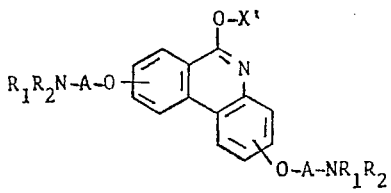

| X' | —O—A—NR$_1$R$_2$ | X' | —O—A—NR$_1$R$_2$ |
|---|---|---|---|
| n—C$_3$H$_7$ | 3,8—OCH$_2$CH$_2$N(C$_2$H$_5$)$_2$ | i—C$_3$H$_7$ | 3,8—OCH$_2$CH(CH$_3$)CH$_2$N(CH$_3$)$_2$ |
| n—C$_6$H$_{13}$ | 3,8—OCH$_2$CH$_2$N(C$_2$H$_5$)$_2$ | CH$_3$ | 3,10—OCH$_2$CH$_2$N(C$_2$H$_5$)$_2$ |
| C$_2$H$_5$ | 3,8—OCH$_2$CH$_2$N(i—C$_3$H$_7$)$_2$ | n—C$_4$H$_9$ | 3,10—OCH$_2$CH$_2$N(C$_2$H$_5$)$_2$ |
| i—C$_3$H$_7$ | 3,8—OCH$_2$CH$_2$N(i—C$_3$H$_7$)$_2$ | C$_2$H$_5$ | 3,9—OCH$_2$CH$_2$N(C$_2$H$_5$)$_2$ |
| CH$_3$ | 3,8—OCH$_2$CH$_2$N(CH$_3$)$_2$ | n—C$_6$H$_{13}$ | 3,9—OCH$_2$CH$_2$N(C$_2$H$_5$)$_2$ |
| n—C$_4$H$_9$ | 3,8—OCH$_2$CH$_2$N(CH$_3$)$_2$ | CH$_3$ | 2,9—OCH$_2$CH$_2$N(C$_2$H$_5$)$_2$ |
| C$_2$H$_5$ | 3,8—OCH$_2$CH$_2$N(n—C$_4$H$_9$)$_2$ | i—C$_3$H$_7$ | 2,9—OCH$_2$CH$_2$N(C$_2$H$_5$)$_2$ |
| CH$_3$ | 3,8—O(CH$_2$)$_3$N(C$_2$H$_5$)$_2$ | CH$_3$ | 3,8—OCH$_2$CH$_2$N(CH$_3$)(n—C$_4$H$_9$) |
| CH$_3$ | 3,8—O(CH$_2$)$_3$N(n—C$_4$H$_9$)$_2$ | CH$_3$ | 3,8—O(CH$_2$)$_6$N(C$_2$H$_5$)$_2$ |
| n—C$_4$H$_9$ | 3,8—O(CH$_2$)$_3$N(n—C$_4$H$_9$)$_2$ | n—C$_6$H$_{13}$ | 3,8—O(CH$_2$)$_6$N(C$_2$H$_5$)$_2$ |
| C$_2$H$_5$ | 3,8—OCH$_2$CH$_2$N(CH$_3$)(C$_2$H$_5$) | CH$_3$ | 3,8—OCH$_2$CH$_2$N(n—C$_6$H$_{13}$)$_2$ |

EXAMPLE XVII

3,8-Bis[(β-Diethylamino)ethoxy]-5Methyl-6(5H)Phenanthridinone

To oil-free sodium hydride (86 mg. of 56%, 2 mM) in N,N-dimethylformamide (20 ml.) was added 3,8-bis[(β-diethylamino)ethoxy]-6(5H)phenanthridinone (425.6 mg., 1.0 mM). The mixture was stirred for one-half hour at room temperature and then a solution of methyl iodide (142 mg., 1.0 mM) in N,N-dimethylformamide (5 ml.) added dropwise over a period of 15 minutes. Stirring was continued overnight and then methyl iodide (14 mg.) added. The mixture was stirred an additional three hours and then poured into water (50 ml.). The product was extracted with ether (75 ml.) and the ethereal extract washed with 1N sodium hydroxide (50 ml.), followed by a water (50 ml.) wash. It was dried (MgSO$_4$) and evaporated in vacuo to give 355 mg. of product: M.P. 58° C.–61° C.

Analysis: Calcd. for: C$_{26}$H$_{37}$N$_3$O$_3$: C, 71.04; H, 8.48; N, 9.56%. Found: C, 70.79; H, 8.38; N, 9.38%.

EXAMPLE XVIII

3,8-Bis[(β-diethylamino)ethoxy]-5-Benzyl-6(5H)Phenanthridinone 3,8-bis[(β-diethylamino)ethoxy]-6(5H)phenanthridinone (425.6 mg., 1.0 mM) was added to a suspension of oil-free sodium hydride (86 mg. of 56%; 2.0 mM) in N,N-dimethylformamide (20 ml.) and the mixture stirred at room temperature for one-half hour. Benzyl chloride (126.6 mg., 1.0 mM) was added over a 15 minute period. The mixture was stirred for 24 hours and then worked up according to the method of Example XVII to give the product (480 mg.): M.P. 64° C.–67° C.

Analysis: Calcd. for C$_{32}$H$_{41}$N$_3$O$_3$: C, 74.53; H, 8.01; N, 8.15%. Found: C, 74.18; H, 7.99; N, 7.74%.

EXAMPLE XIX

The following compounds are prepared from benzyl chloride and appropriate alkyl halides and from appropriate phenanthridinone reactants of Examples I - VI by the procedurce of Examples XVII and XVIII.

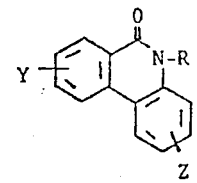

| R | Y = Z | R | Y = Z |
|---|---|---|---|
| n—C$_2$H$_5$ | 3,8—OCH$_2$CH$_2$N(C$_2$H$_5$)$_2$ | n—C$_3$H$_7$ | 3,8—OCH$_2$CH$_2$N(n—C$_6$H$_{13}$)$_2$ |
| n—C$_4$H$_9$ | 3,8—OCH$_2$CH$_2$N(C$_2$H$_5$)$_2$ | CH$_3$ | 3,8—O(CH$_2$)$_6$N(C$_2$H$_5$)$_2$ |
| n—C$_6$H$_{13}$ | 3,8—OCH$_2$CH$_2$N(C$_2$H$_5$)$_2$ | n—C$_4$H$_9$ | 3,8—O(CH$_2$)$_6$N(C$_2$H$_5$)$_2$ |
| CH$_3$ | 3,8—OCH$_2$CH$_2$N(CH$_3$)$_2$ | n—C$_6$H$_{13}$ | 3,8—O(CH$_2$)$_6$N(C$_2$H$_5$)$_2$ |
| i—C$_3$H$_7$ | 3,8—OCH$_2$CH$_2$N(CH$_3$)$_2$ | CH$_3$ | 3,10—OCH$_2$CH$_2$N(C$_2$H$_5$)$_2$ |
| C$_2$H$_5$ | 3,8—OCH$_2$CH$_2$N(i—C$_3$H$_7$)$_2$ | n—C$_4$H$_9$ | 3,10—OCH$_2$CH$_2$N(C$_2$H$_5$)$_2$ |
| n—C$_4$H$_9$ | 3,8—OCH$_2$CH$_2$N(i—C$_3$H$_7$)$_2$ | C$_2$H$_5$ | 3,9—OCH$_2$CH$_2$N(C$_2$H$_5$)$_2$ |
| CH$_3$ | 3,8—OCH$_2$CH$_2$N(n—C$_3$H$_7$)$_2$ | CH$_3$ | 2,9—OCH$_2$CH$_2$N(C$_2$H$_5$)$_2$ |
| C$_2$H$_5$ | 3,8—O(CH$_2$)$_3$N(CH$_3$)$_2$ | n—C$_4$H$_9$ | 2,9—OCH$_2$CH$_2$N(C$_2$H$_5$)$_2$ |
| n—C$_5$H$_{11}$ | 3,8—O(CH$_2$)$_3$N(CH$_3$)$_2$ | C$_7$H$_7$ | 2,9—OCH$_2$CH$_2$N(C$_2$H$_5$)$_2$ |
| CH$_3$ | 3,8—O(CH$_2$)$_3$N(n—C$_4$H$_9$)$_2$ | CH$_3$ | 3,8—O(CH$_2$)$_3$N(C$_2$H$_5$)$_2$ |
| n—C$_3$H$_7$ | 3,8—O(CH$_2$)$_3$N(n—C$_4$H$_9$)$_2$ | C$_7$H$_7$ | 3,8—O(CH$_2$)$_3$N(C$_2$H$_5$)$_2$ |
| C$_2$H$_5$ | 3,8—OCH$_2$CH$_2$N(CH$_3$)(C$_2$H$_5$) | C$_7$H$_7$ | 3,8—OCH$_2$CH$_2$N(C$_2$H$_5$)$_2$ |
| C$_2$H$_5$ | 3,8—OCH$_2$CH$_2$N(CH$_3$)-(n—C$_4$H$_9$) | C$_7$H$_7$ | 3,8—O(CH$_2$)$_6$N(C$_2$H$_5$)$_2$ |
| CH$_3$ | 3,8—OCH$_2$CH(CH$_3$)CH$_2$N(CH$_3$)$_2$ | C$_7$H$_7$ | 3,8—OCH$_2$CH$_2$N(n—C$_6$H$_{13}$)$_2$ |

-continued

| R | Y = Z | R | Y = Z |
|---|---|---|---|
| n—C$_6$H$_{13}$ | 3,8—OCH$_2$CH(CH$_3$)CH$_2$N(CH$_3$)$_2$ | C$_7$H$_7$ | 3,8—OCH$_2$CH(CH$_3$)CH$_2$N(CH$_3$)$_2$ |
| CH$_3$ | 3,8—OCH$_2$CH$_2$N(n—C$_6$H$_{13}$)$_2$ | C$_7$H$_7$ | 3,10—OCH$_2$CH$_2$N(C$_2$H$_5$)$_2$ |
| n—C$_6$H$_{13}$ | 3,8—OCH$_2$CH$_2$N(n—C$_6$H$_{13}$)$_2$ | C$_7$H$_7$ | 3,9—OCH$_2$CH$_2$N(C$_2$H$_5$)$_2$ |

Compounds having the above formula wherein one of Y or Z is hydrogen prepared by this process are listed below.

| R | Z (Y = H) | R | Y (Z = H) |
|---|---|---|---|
| CH$_3$ | 8—OCH$_2$CH$_2$N(C$_2$H$_5$)$_2$ | CH$_3$ | 3—OCH$_2$CH$_2$N(C$_2$H$_5$)$_2$ |
| n—C$_4$H$_9$ | 8—OCH$_2$CH$_2$N(C$_2$H$_5$)$_2$ | n—C$_3$H$_7$ | 3—OCH$_2$CH$_2$N(C$_2$H$_5$)$_2$ |
| C$_7$H$_7$ | 8—OCH$_2$CH$_2$N(C$_2$H$_5$)$_2$ | n—C$_6$H$_{13}$ | 3—OCH$_2$CH$_2$N(C$_2$H$_5$)$_2$ |
| C$_2$H$_5$ | 9—OCH$_2$CH$_2$N(C$_2$H$_5$)$_2$ | C$_7$H$_7$ | 3—OCH$_2$CH$_2$N(C$_2$H$_5$)$_2$ |
| i—C$_3$H$_7$ | 9—OCH$_2$CH$_2$N(C$_2$H$_5$)$_2$ | C$_2$H$_5$ | 2—OCH$_2$CH$_2$N(C$_2$H$_5$)$_2$ |
| C$_7$H$_7$ | 9—OCH$_2$CH$_2$N(C$_2$H$_5$)$_2$ | C$_7$H$_7$ | 2—OCH$_2$CH$_2$N(C$_2$H$_5$)$_2$ |
| CH$_3$ | 10—OCH$_2$CH$_2$N(C$_2$H$_5$)$_2$ | CH$_3$ | 1—OCH$_2$CH$_2$N(C$_2$H$_5$)$_2$ |
| n—C$_5$H$_{11}$ | 10—OCH$_2$CH$_2$N(C$_2$H$_5$)$_2$ | n—C$_4$H$_9$ | 1—OCH$_2$CH$_2$N(C$_2$H$_5$)$_2$ |
| C$_7$H$_7$ | 10—OCH$_2$CH$_2$N(C$_2$H$_5$)$_2$ | C$_7$H$_7$ | 1—OCH$_2$CH$_2$N(C$_2$H$_5$)$_2$ |
| C$_2$H$_5$ | 8—OCH$_2$CH$_2$N(CH$_3$)$_2$ | C$_2$H$_5$ | 3—OCH$_2$CH$_2$N(CH$_3$)$_2$ |
| n—C$_4$H$_9$ | 8—OCH$_2$CH$_2$N(CH$_3$)$_2$ | n—C$_6$H$_{13}$ | 3—OCH$_2$CH$_2$N(CH$_3$)$_2$ |
| C$_7$H$_7$ | 8—OCH$_2$CH$_2$N(CH$_3$)$_2$ | C$_7$H$_7$ | 3—OCH$_2$CH$_2$N(CH$_3$)$_2$ |
| CH$_3$ | 9—OCH$_2$CH$_2$N(CH$_3$)$_2$ | C$_2$H$_5$ | 2—OCH$_2$CH$_2$N(CH$_3$)$_2$ |
| n—C$_3$H$_7$ | 9—OCH$_2$CH$_2$N(CH$_3$)$_2$ | C$_7$H$_7$ | 2—OCH$_2$CH$_2$N(CH$_3$)$_2$ |
| CH$_3$ | 10—OCH$_2$CH$_2$N(CH$_3$)$_2$ | CH$_3$ | 1—OCH$_2$CH$_2$N(CH$_3$)$_2$ |
| C$_7$H$_7$ | 10—OCH$_2$CH$_2$N(CH$_3$)$_2$ | n—C$_4$H$_9$ | 1—OCH$_2$CH$_2$N(CH$_3$)$_2$ |
| CH$_3$ | 8—O(CH$_2$)$_3$N(CH$_3$)$_2$ | CH$_3$ | 3—O(CH$_2$)$_3$N(CH$_3$)$_2$ |
| i—C$_3$H$_7$ | 8—O(CH$_2$)$_3$N(CH$_3$)$_2$ | i—C$_3$H$_7$ | 3—O(CH$_2$)$_3$N(CH$_3$)$_2$ |
| C$_7$H$_7$ | 8—O(CH$_2$)$_3$N(CH$_3$)$_2$ | C$_7$H$_7$ | 3—O(CH$_2$)$_3$N(CH$_3$)$_2$ |
| CH$_3$ | 9—O(CH$_2$)$_3$N(CH$_3$)$_2$ | C$_2$H$_5$ | 2—O(CH$_2$)$_3$N(CH$_3$)$_2$ |
| n—C$_3$H$_7$ | 10—O(CH$_2$)$_3$N(CH$_3$)$_2$ | CH$_3$ | 1—O(CH$_2$)$_3$N(CH$_3$)$_2$ |
| CH$_3$ | 8—OCH$_2$CH$_2$N(CH$_3$)(C$_2$H$_5$) | CH$_3$ | 3—OCH$_2$CH$_2$N(CH$_3$)(C$_2$H$_5$) |
| C$_7$H$_7$ | 8—OCH$_2$CH$_2$N(CH$_3$)(C$_2$H$_5$) | n—C$_3$H$_7$ | 3—OCH$_2$CH$_2$N(CH$_3$)(C$_2$H$_5$) |
| n—C$_6$H$_{13}$ | 8—OCH$_2$CH$_2$N(CH$_3$)(C$_2$H$_5$) | n—C$_5$H$_{11}$ | 3—OCH$_2$CH$_2$N(CH$_3$)(C$_2$H$_5$) |
| CH$_3$ | 8—O(CH$_2$)$_3$N(i—C$_3$H$_7$)$_2$ | CH$_3$ | 3—O(CH$_2$)$_3$N(i—C$_3$H$_7$)$_2$ |
| C$_7$H$_7$ | 8—O(CH$_2$)$_3$N(i—C$_3$H$_7$)$_2$ | C$_7$H$_7$ | 3—O(CH$_2$)$_3$N(i—C$_3$H$_7$)$_2$ |
| CH$_3$ | 8—O(CH$_2$)$_6$N(C$_2$H$_5$)$_2$ | CH$_3$ | 3—O(CH$_2$)$_6$N(C$_2$H$_5$)$_2$ |
| n—C$_4$H$_9$ | 8—O(CH$_2$)$_6$N(C$_2$H$_5$)$_2$ | C$_2$H$_5$ | 3—O(CH$_2$)$_6$N(C$_2$H$_5$)$_2$ |
| C$_7$H$_7$ | 8—O(CH$_2$)$_6$N(C$_2$H$_5$)$_2$ | n—C$_6$H$_{13}$ | 3—O(CH$_2$)$_6$N(C$_2$H$_5$)$_2$ |
| CH$_3$ | 8—OCH$_2$CH$_2$N(n—C$_6$H$_{13}$)$_2$ | C$_7$H$_7$ | 3—O(CH$_2$)$_6$N(C$_2$H$_5$)$_2$ |
| n—C$_6$H$_{13}$ | 8—OCH$_2$CH$_2$N(n—C$_6$H$_{13}$)$_2$ | C$_7$H$_7$ | 3—OCH$_2$CH$_2$N(n—C$_6$H$_{13}$)$_2$ |
| C$_7$H$_7$ | 8—OCH$_2$CH$_2$N(n—C$_6$H$_{13}$)$_2$ | CH$_3$ | 3—OCH$_2$CH$_2$N(n—C$_6$H$_{13}$)$_2$ |
| CH$_3$ | 9—OCH$_2$CH(CH$_3$)CH$_2$N(CH$_3$)$_2$ | n—C$_5$H$_{11}$ | 3—OCH$_2$CH$_2$N(n—C$_6$H$_{13}$)$_2$ |
| n—C$_3$H$_7$ | 9—OCH$_2$CH(CH$_3$)CH$_2$N(CH$_3$)$_2$ | C$_2$H$_5$ | 2—OCH$_2$CH(CH$_3$)CH$_2$N(CH$_3$)$_2$ |
| n—C$_5$H$_{11}$ | 9—OCH$_2$CH(CH$_3$)CH$_2$N(CH$_3$)$_2$ | n—C$_6$H$_{13}$ | 2—OCH$_2$CH(CH$_3$)CH$_2$N(CH$_3$)$_2$ |
| C$_7$H$_7$ | 9—OCH$_2$CH(CH$_3$)CH$_2$N(CH$_3$)$_2$ | C$_7$H$_7$ | 2—OCH$_2$CH(CH$_3$)CH$_2$N(CH$_3$)$_2$ |
| CH$_3$ | 7—OCH$_2$CH$_2$N(C$_2$H$_5$)$_2$ | C$_7$H$_7$ | 4—OCH$_2$CH$_2$N(C$_2$H$_5$)$_2$ |
| n—C$_4$H$_9$ | 7—OCH$_2$CH$_2$N(C$_2$H$_5$)$_2$ | CH$_3$ | 4—OCH$_2$CH$_2$N(C$_2$H$_5$)$_2$ |
| n—C$_6$H$_{13}$ | 7—OCH$_2$CH$_2$N(C$_2$H$_5$)$_2$ | n—C$_3$H$_7$ | 4—OCH$_2$CH$_2$N(C$_2$H$_5$)$_2$ |
| C$_7$H$_7$ | 7—OCH$_2$CH$_2$N(C$_2$H$_5$)$_2$ | n—C$_6$H$_{13}$ | 4—OCH$_2$CH$_2$N(C$_2$H$_5$)$_2$ |

EXAMPLE XX 3,8-Bis[(β-Diisopropylamino(ethoxy]-5-(β-Diethylaminoethyl)-6(5H)Phenanthridinone Oil-free sodium hydride (53.5 mq. of 56%, 1.25 nM); N,N-dimethylformamide (5 mil.), 92.5 mg., 0.685 mM) and 3,8-bis[(β-diisopropylamino)ethoxy]-6(5H)phenanthridinone (300 mg., 0.625 mM) were reacted according to the procedure of Example XVII to give 300 mg. of the title product.

Analysis: Calcd. for C$_{35}$H$_{56}$N$_4$O$_3$: C, 72.37; H, 9.72; N. 9.65%. Found: C, 72.16; H, 9.43; N, 9.52%.

EXAMPLE XXI

5-[(β-Diethylamino)ethyl]-8-[(β-diethylamino)ethoxy]-6(5H)Phenanthridinone

A mixture of oil-free sodium hydride (86 mg. of 56%, 2 mM), N,N-dimethylformamide (5 ml.), 8-[(β-diethylamino(ethoxy]-6(5H)phenanthridinone (310.4 mg., 1 mM) and β-diethylaminoethylchloride was reacted according to the procedure of Example XVII to give 380 mg. of the title product.

Analysis: Calcd. for C$_{25}$H$_{35}$N$_3$O$_2$: C, 73.31; H, 8.61 N, 10.20%. Found: C, 72,86; H, 8.38; N, 10.02%.

EXAMPLE XXII

3-[(β-Diethylamino)ethoxy]-5-[(β-diethylamino)ethyl]-6(5H)Phenanthridinone

Oil-free sodium hydride (86 mg. of 56%; 2 mM); N,N-dimethylformamide (5 ml.), 3-[(β-diethylamino)ethoxy]-6(5H)phenanthridinone (230 mg., 0.742 mM) and β-diethylamino chloride (110 mg., 0.82 mM) were reacted according to the procedure of Example XVII to produce 250 mg. of the title product as an oil.

Analysis: Calcd. for C$_{25}$H$_{35}$N$_3$O$_2$: C, 73.31; H, 8.61; N, 10.26%. Found : C, 71.72; H, 8.46; N, 9.64%.

EXAMPLE XXIII

Repetition of the procedure of Examples XX–XXII but using the appropriate phenanthridinones of Examples I–VI and the appropriate ω-dialkyl aminoalkyl chloride reactants affords the following compounds:

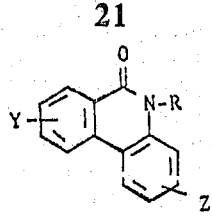

| R | Y = Z |
|---|---|
| CH₂CH₂N(C₂H₅)₂ | 3,8—OCH₂CH₂N(C₂H₅)₂ |
| (CH₂)₃N(CH₃)₂ | 3,8—OCH₂CH₂N(C₂H₅)₂ |
| (CH₂)₆N(CH₃)₂ | 3,8—OCH₂CH₂N(C₂H₅)₂ |
| CH(C₂H₅)(CH₂)₃N(C₂H₅)₂ | 3,8—OCH₂CH₂N(C₂H₅)₂ |
| CH₂CH₂N(CH₃)₂ | 3,8—OCH₂CH₂N(CH₃)₂ |
| (CH₂)₄N(i—C₃H₇)₂ | 3,8—OCH₂CH₂N(CH₃)₂ |
| CH₂CH₂N(n—C₆H₁₃)₂ | 3,8—O(CH₂)₃N(CH₃)₂ |
| (CH₂)₆N(C₂H₅)₂ | 3,8—O(CH₂)₃N(CH₃)₂ |
| CH₂CH₂N(CH₃)₂ | 3,8—OCH₂CH₂N(CH₃)(C₂H₅) |
| CH₂CH₂N(C₂H₅)₂ | 3,8—OCH₂CH₂N(n—C₄H₉)₂ |
| (CH₂)₄N(C₂H₅)₂ | 3,8—OCH₂CH₂N(n—C₄H₉)₂ |
| CH₂CH₂N(CH₃)₂ | 3,8—O(CH₂)₆N(C₂H₅)₂ |
| CH(C₄H₉)CH₂N(n—C₄H₉)₂ | 3,8—O(CH₂)₆N(C₂H₅)₂ |
| CH₂CH₂N(n—C₆H₁₃)₂ | 3,8—OCH₂CH₂N(n—C₆H₁₃)₂ |
| CH(CH₃)CH₂N(CH₃)₂ | 3,8—OCH₂CH(CH₃)CH₂N(CH₃)₂ |
| (CH₂)₄N(C₂H₅)₂ | 3,8—OCH₂CH(CH₃)CH₂N(CH₃)₂ |
| CH₂CH₂N(C₂H₅)₂ | 3,10—OCH₂CH₂N(C₂H₅)₂ |
| (CH₂)₄N(i—C₃H₇)₂ | 3,10—OCH₂CH₂N(C₂H₅)₂ |
| CH(C₄H₉)CH₂N(n—C₄H₉)₂ | 3,10—OCH₂CH₂N(C₂H₅)₂ |
| (CH₂)₃N(CH₃)₂ | 3,9—OCH₂CH₂N(C₂H₅)₂ |
| CH₂CH₂N(n—C₄H₉)₂ | 3,9—OCH₂CH₂N(C₂H₅)₂ |
| CH₂CH₂N(CH₃)₂ | 2,9—OCH₂CH₂N(C₂H₅)₂ |
| (CH₂)₄N(C₂H₅)₂ | 2,9—OCH₂CH₂N(C₂H₅)₂ |
| CH₂CH₂N(n—C₆H₁₃)₂ | 2,9—OCH₂CH₂N(C₂H₅)₂ |
| CH₂CH₂N(C₂H₅)₂ | 3,8—O(CH₂)₃N(n—C₄H₉)₂ |
| (CH₂)₆N(CH₃)₂ | 3,8—O(CH₂)₃N(n—C₄H₉)₂ |
| CH₂CH₂N(C₂H₅)₂ | 3,8—OCH₂CH₂N(i—C₃H₇)₂ |
| (CH₂)₆N(CH₃)₂ | 3,8—OCH₂CH₂N(n—C₆H₁₃)₂ |

Compounds having the above formula wherein one of Y or Z is hydrogen prepared by this process are listed below.

| R | Z (Y = H) |
|---|---|
| CH₂CH₂N(C₂H₅)₂ | 8—OCH₂CH₂N(C₂H₅)₂ |
| (CH₂)₄N(C₂H₅)₂ | 8—OCH₂CH₂N(C₂H₅)₂ |
| (CH₂)₆N(C₂H₅)₂ | 8—OCH₂CH₂N(C₂H₅)₂ |
| CH₂CH₂N(CH₃)₂ | 9—OCH₂CH₂N(C₂H₅)₂ |
| (CH₂)₄N(C₂H₅)₂ | 9—OCH₂CH₂N(C₂H₅)₂ |
| CH₂CH₂N(CH₃)₂ | 10—OCH₂CH₂N(C₂H₅)₂ |
| (CH₂)₄N(i—C₃H₇)₂ | 8—OCH₂CH₂N(CH₃)₂ |
| (CH₂)₄N(CH₃)₂ | 9—OCH₂CH₂N(CH₃)₂ |
| CH(C₂H₅)(CH₂)₃N(C₂H₅)₂ | 10—OCH₂CH₂N(CH₃)₂ |
| CH₂CH₂N(n—C₆H₁₃)₂ | 8—O(CH₂)₃N(CH₃)₂ |
| CH(C₄H₉)CH₂N(n—C₄H₉)₂ | 8—O(CH₂)₃N(CH₃)₂ |
| CH₂CH₂N(C₂H₅)₂ | 9—O(CH₂)₃N(CH₃)₂ |
| (CH₂)₃N(CH₃)₂ | 8—O(CH₂)₂N(CH₃)(C₂H₅) |
| (CH₂)₆N(CH₃)₂ | 8—O(CH₂)₃N(CH₃)(C₂H₅) |
| (CH₂)₄N(C₂H₅)₂ | 8—OCH₂CH₂N(i—C₃H₇)₂ |
| CH₂CH₂N(C₂H₅)₂ | 8—O(CH₂)₆N(C₂H₅)₂ |
| (CH₂)₆N(C₂H₅)₂ | 8—O(CH₂)₆N(C₂H₅)₂ |
| CH₂CH₂N(CH₃)₂ | 8—OCH₂CH₂N(n—C₆H₁₃)₂ |
| (CH₂)₃N(C₂H₅)₂ | 8—OCH₂CH₂N(n—C₆H₁₃)₂ |
| (CH₂)₃N(C₂H₅)₂ | 9—OCH₂CH(CH₃)CH₂N(CH₃)₂ |
| CH₂CH(CH₃)N(CH₃)₂ | 9—OCH₂CH(CH₃)CH₂N(CH₃)₂ |
| CH(C₄H₉)CH₂N(n—C₄H₉)₂ | 7—OCH₂CH₂N(C₂H₅)₂ |
| CH₂CH₂N(C₂H₅)₂ | 7—OCH₂CH₂N(C₂H₅)₂ |
| CH₂CH₂N(n—C₆H₁₃)₂ | 7—OCH₂CH₂N(C₂H₅)₂ |
| R | Y (Z = H) |
| CH₂CH₂N(C₂H₅)₂ | 3—OCH₂CH₂N(C₂H₅)₂ |
| (CH₂)₄N(C₂H₅)₂ | 3—OCH₂CH₂N(C₂H₅)₂ |
| (CH₂)₆N(C₂H₅)₂ | 3—OCH₂CH₂N(C₂H₅)₂ |
| CH₂CH₂N(CH₃)₂ | 2—OCH₂CH₂N(C₂H₅)₂ |
| (CH₂)₄N(C₂H₅)₂ | 2—OCH₂CH₂N(C₂H₅)₂ |
| CH₂CH₂N(CH₃)₂ | 1—OCH₂CH₂N(C₂H₅)₂ |
| (CH₂)₃N(CH₃)₂ | 3—OCH₂CH₂N(CH₃)₂ |
| (CH₂)₆N(CH₃)₂ | 2—OCH₂CH₂N(CH₃)₂ |
| CH(C₂H₅)(CH₂)₃N(C₂H₅)₂ | 1—OCH₂CH₂N(CH₃)₂ |
| CH₂CH₂N(n—C₆H₁₃)₂ | 3—O(CH₂)₅N(CH₃)₂ |
| CH(C₄H₉)CH₂N(n—C₄H₉)₂ | 3—O(CH₂)₃N(CH₃)₂ |
| CH₂CH(CH₃)N(CH₃)₂ | 3—O(CH₂)₃N(CH₃)₂ |
| (CH₂)₄N(i—C₃H₇)₂ | 2—O(CH₂)₃N(CH₃)₂ |
| CH₂CH₂N(CH₃)₂ | 1—O(CH₂)₃N(CH₃)₂ |
| CH₂CH₂N(C₂H₅)₂ | 3—OCH₂CH₂N(CH₃)(C₂H₅) |
| CH₂CH₂N(CH₃)₂ | 3—O(CH₂)₆N(C₂H₅)₂ |
| (CH₂)₄N(C₂H₅)₂ | 3—O(CH₂)₆N(C₂H₅)₂ |
| (CH₂)₃N(C₂H₅)₂ | 3—OCH₂CH₂N(n—C₆H₁₃)₂ |
| CH₂CH₂N(n—C₆H₁₃)₂ | 3—OCH₂CH₂N(n—C₆H₁₃)₂ |
| (CH₂)₆N(C₂H₅)₂ | 3—OCH₂CH₂N(n—C₆H₁₃)₂ |
| CH₂CH(CH₃)N(CH₃)₂ | 2—OCH₂CH(CH₃)CH₂N(CH₃)₂ |
| CH₂CH₂N(C₂H₅)₂ | 4—OCH₂CH₂N(C₂H₅)₂ |
| (CH₂)₄N(C₂H₅)₂ | 4—OCH₂CH₂N(C₂H₅)₂ |
| (CH₂)₆N(C₂H₅)₂ | 4—OCH₂CH₂N(C₂H₅)₂ |

What is claimed is:

1. A process for the induction of endogeneous interferon in vertebrate animals which comprises orally, parenterally, intranasally or topically administering to the animals a composition containing as the essential active ingredient an effective amount of a compound selected from the group consisting of those having the formulae

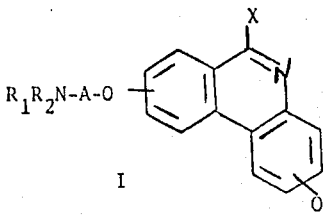

and the pharmaceutically-acceptable acid addition salts thereof wherein X is selected from the group consisting of chloro, bromo, hydroxy, alkoxy containing from 1 to 6 carbon atoms, amino, monoalkylamino, dialkylamino wherein each of the alkyl groups contains from 1 to 6 carbon atoms, and benzylamino;

R is selected from the group consisting of hydrogen, alkyl containing from 1 to 6 carbon atoms, —A—NR₁R₂ wherein each of R₁ and R₂ is alkyl containing from 1 to 6 carbon atoms and A is a divalent alkylene radical containing from 2 to 6 carbon atoms; and each of Y and Z is selected from the group consisting of hydrogen, and ω-dialkylaminoalkoxy wherein the alkyl and alkoxy groups contain from 1 to 6 carbon atoms, respectively;

with the proviso that when R is hydrogen or alkyl, each of Y and Z is ω-dialkylaminoalkoxy.

2. A process according to claim 1 wherein the compound is of formula I.

3. A process according to claim 1 wherein the compound is of formula II.

4. A process according to claim 3 wherein the compound is 3,8-bis[(β-diethylamino)ethoxy]-6(5H)-phenanthridinone, a compound of formula II wherein each of Y and Z is [(β-diethylamino)ethoxy]-; and R is hydrogen.

5. A process according to claim 3 wherein the compound is 3-[(β-diethylamino)ethoxy]-5-[(β-diethylamino)ethyl]-6(5H)-phenanthridinone, a compound of formula II wherein Y is hydrogen; R is [(β- diethylamino)-ethyl]-; and Z is [(β-diethylamino)ethoxy]-.

6. A process according to claim 3 wherein the compound is 5-(β-diethylamino)ethyl]-8-[(β-diethylamino)ethoxy]-6(5H)-phenanthridinone, a compound of formula II wherein Z is hydrogen; R is [(β-diethylamino)ethyl]-; and Y is [(β-diethylamino)ethoxy]-.

7. A pharmaceutical composition active as an antiviral agent comprising a pharmaceutical diluent and an effective amount of a compound selected from the group consisting of those having the formulae

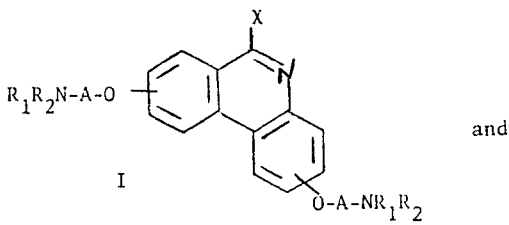

and

I

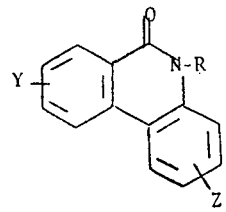

II wherein X is selected from the group consisting of chloro, bromo, hydroxy, alkoxy containing from 1 to 6 carbon atoms, amino, monoalkylamino, dialkylamino wherein each of the alkyl groups contains from 1 to 6 carbon atoms, and benzylamino;

R is selected from the group consisting of hydrogen, alkyl containing from 1 to 6 carbon atoms, —A—NR$_1$R$_2$ wherein each of R$_1$ and R$_2$ is alkyl containing from 1 to 6 carbon atoms and A is a divalent alkylene radical containing from 2 to 6 carbon atoms;

each of Y and Z is selected from the group consisting of hydrogen, and ω-dialkylaminoalkoxy wherein the alkyl and alkoxy groups contains from 1 to 6 carbon atoms, and from 2 to 6 carbon atoms, respectively with the proviso that when R is hydrogen or alkyl, each of Y and Z is ω-dialkylaminoalkoxy.

8. A composition according to claim 7 wherein the compound is of formula I.

9. A composition according to claim 7 wherein the compound is of formula II.

10. A composition according to claim 9 wherein the compound is 3,8-bis[(β-diethylamino)ethoxy]-6(5H)-phenanthridinone, a compound of formula II wherein each of Y and Z is [(β-diethylamino)ethoxy]-; and R is hydrogen.

11. A composition according to claim 9 wherein the compound is 3-[(β-diethylamino)ethoxy]-5-[β-diethylaminolethyl]-6(5H)-phenanthridinone, a compound of formula II wherein Y is hydrogen; Z is [(β-diethylamino)ethoxy]-, and R is [(β-diethylamino)ethyl-.

* * * * *

UNITED STATES PATENT OFFICE
CERTIFICATE OF CORRECTION

PATENT NO. : 3,932,643

DATED : January 13, 1976

INVENTOR(S) : George J. Gauthier

It is certified that error appears in the above-identified patent and that said Letters Patent are hereby corrected as shown below:

Col. 1, line 19, "production of" should read -- production in --

Col. 2, line 39, "to huge" should read -- for huge --

Col. 3, line 54, "(4,4- " should read -- (4,4'- --

Col. 3, line 55, "(1,1- " should read -- (1,1'- --

Col. 3, line 62, "variety in vivo" should read -- variety of viruses in vivo --

Col. 4, line 7, "along are" should read -- alone are --

Col. 4, line 37, "hydrozoic acid" should read -- hydrazoic acid --

Col. 4, line 40, "aside or hydrazoic zcid" should read -- azide or hydrazoic acid --

Col. 4, line 55, "hydrozoic acid" should read -- hydrazoic acid --

Col. 4, line 57, "acis is" should read -- acid is --

Col. 4, line 59, "acid used" should read -- acid are used --

Col. 5, line 61, "phenanthridinone the" should read -- phenanthridinone with the --

Col. 6, line 25, "6-halo to by" should read -- 6-halo atom by --

Col. 6, line 25, "substituted is" should read -- substituted amino is --

Col. 9 , line 63, "25 to 48" should read -- 24 to 48 --

Col. 10, line 51, "ehtoxy]-" should read -- ethoxy]- --

Col. 10, line 55, "...amino-ethoxy]..." should read -- ...amino)ethoxy]... --

Col. 12, line 23, "propxy]" should read -- propoxy] --

Col. 12, line 39, "2,7-" should read -- 2.7 --

Col. 13, line 4, "...amino(ethoxy]... " should read -- ...amino)ethoxy]... --

Col. 14, line 42, "...amino(ethoxy]..." should read -- ...amino)ethoxy]... --

UNITED STATES PATENT OFFICE
CERTIFICATE OF CORRECTION

PATENT NO. : 3,932,643

DATED : January 13, 1976

INVENTOR(S) : George J. Gauthier

It is certified that error appears in the above-identified patent and that said Letters Patent are hereby corrected as shown below:

Col. 14, line 46, "...amino(ethoxy]..." should read -- ...amino)ethoxy]... --

Col. 15, line 31, "thiethylamine" should read -- triethylamine --

Col. 15, line 41, "ethoxy-9" should read -- ethoxy]- --

Col. 16, line 25, "10.85%" should read -- 10.88% --

Col. 16, in the table following the structural formula, "$(n-C_3H_7)_2$" shown below the table should appear immediately following "$3,8-OCH_2CH_2N-$" in the last line of said table.

Col. 17, line 8, "$C_{26}H_{37}N_3 1/2\ H_2O$:" should read -- $C_{26}H_{37}N_3O_3 1/2\ H_2O$: --

Col. 18, line 9, "8.38" should read -- 8.37 --

Col. 19, line 50, "...amino(ethoxy]..." should read -- ...amino)ethoxy]... --

Col. 19, line 53, "(53.5 mq. of 56%, 1.25 nM)" should read -- (53.5 mg. of 56%, 1.25 mM) --

Col. 19, line 54, "(5 mil.) 92.5" should read -- (5 mil.) β-diethylaminoethylchloride (92.5 --

Col. 19, line 67, "thylamino(ethoxy]-6(5H)phenantridinone" should read -- thylamino)ethoxy]-6(5H)phenanthridinone --

Col. 22, lines 52-53, "from 1 to 6 carbon atoms," should read -- from 1 to 6 carbon atoms and from 2 to 6 carbon atoms, -- .

Signed and Sealed this sixth Day of April 1976

[SEAL]

Attest:

RUTH C. MASON
Attesting Officer

C. MARSHALL DANN
Commissioner of Patents and Trademarks